(12) United States Patent
De Haan et al.

(10) Patent No.: US 8,399,728 B2
(45) Date of Patent: Mar. 19, 2013

(54) ABSORBER DEMETHANIZER FOR METHANOL TO OLEFINS PROCESS

(75) Inventors: Stephen De Haan, Wayne, NJ (US); Peter Daniel Kuzma, Jr., Bloomingdale, NJ (US)

(73) Assignee: Lummus Technology Inc., Bloomfield, NJ (US)

( * ) Notice: Subject to any disclaimer, the term of this patent is extended or adjusted under 35 U.S.C. 154(b) by 660 days.

(21) Appl. No.: 12/260,751

(22) Filed: Oct. 29, 2008

(65) Prior Publication Data
US 2010/0105973 A1 Apr. 29, 2010

(51) Int. Cl.
*C07C 1/20* (2006.01)
*C07C 7/08* (2006.01)

(52) U.S. Cl. ........ 585/638; 585/327; 585/324; 585/639; 585/640; 585/800

(58) Field of Classification Search .................. 585/324, 585/327, 638, 639, 640, 800
See application file for complete search history.

(56) References Cited

U.S. PATENT DOCUMENTS

| | | | |
|---|---|---|---|
| 2,610,704 A * | 9/1952 | Patterson | ........................ 95/173 |
| 2,804,488 A | 8/1957 | Cobb, Jr. | |
| 2,849,371 A | 8/1958 | Gilmore | |
| 3,911,041 A | 10/1975 | Kaeding et al. | |
| 4,049,573 A | 9/1977 | Kaeding | |
| 4,062,905 A | 12/1977 | Chang et al. | |
| 4,076,796 A | 2/1978 | Reh et al. | |
| 4,079,095 A | 3/1978 | Givens et al. | |
| 4,499,327 A | 2/1985 | Kaiser | |
| 4,709,113 A | 11/1987 | Harandi et al. | |
| 4,777,321 A | 10/1988 | Harandi et al. | |
| 4,831,195 A | 5/1989 | Harandi et al. | |
| 4,857,667 A | 8/1989 | Harandi et al. | |
| 5,019,143 A | 5/1991 | Mehra | |
| 5,026,529 A | 6/1991 | Harandi et al. | |
| 5,028,400 A | 7/1991 | Harandi et al. | |
| 5,326,929 A | 7/1994 | Mehra et al. | |
| 5,502,971 A | 4/1996 | McCarthy et al. | |
| 5,520,724 A | 5/1996 | Bauer et al. | |
| 5,546,764 A * | 8/1996 | Mehra | ............................. 62/625 |

(Continued)

FOREIGN PATENT DOCUMENTS

| | | |
|---|---|---|
| CN | 1847203 A | 10/2006 |
| CN | 101225013 A | 7/2008 |

(Continued)

OTHER PUBLICATIONS

International Search Report and Written Opinion dated Feb. 22, 2010 in PCT/US2009/046736 (10 pgs.).

(Continued)

*Primary Examiner* — Thuan D Dang
(74) *Attorney, Agent, or Firm* — Osha • Liang LLP

(57) ABSTRACT

A process for conversion of methanol to olefins (MTO), including: contacting methanol and air in a methanol-to-olefins reactor; recovering an effluent from the methanol-to-olefins reactor comprising methanol, ethylene, and nitrogen oxides; separating the effluent via one or more reactive distillation and/or distillation stages using a hydrocarbon absorbent to recover a first fraction comprising ethylene and a second fraction comprising methane; wherein the separating comprises operating the one or more extractive distillation and/or distillation stages at temperatures and pressures sufficient to prevent any substantial conversion of nitrogen oxides to $N_2O_3$.

23 Claims, 1 Drawing Sheet

U.S. PATENT DOCUMENTS

| | | | |
|---|---|---|---|
| 6,212,905 | B1 | 4/2001 | Kuechler et al. |
| 6,287,522 | B1 | 9/2001 | Lomas |
| 7,102,048 | B2 | 9/2006 | Van Egmond et al. |
| 7,166,757 | B2 | 1/2007 | Fung et al. |
| 7,273,542 | B2 | 9/2007 | Duhon et al. |
| 7,923,591 | B2 | 4/2011 | Birke et al. |
| 2004/0116757 | A1* | 6/2004 | Van Egmond et al. ....... 585/324 |
| 2005/0033098 | A1 | 2/2005 | Sumner et al. |
| 2005/0033104 | A1* | 2/2005 | van Egmond et al. ........ 585/800 |
| 2007/0260103 | A1 | 11/2007 | Verma et al. |
| 2008/0154077 | A1 | 6/2008 | Bozzano et al. |
| 2011/0071332 | A1 | 3/2011 | Stanley et al. |

FOREIGN PATENT DOCUMENTS

| | | |
|---|---|---|
| CN | 101250080 A | 8/2008 |

OTHER PUBLICATIONS

PCT Notification Concerning Transmittal of International Preliminary Report on Patentability issued May 3, 2011 in corresponding International Application No. PCT/US2009/046736 (5 pages).

Summary of Official Letter dated Nov. 29, 2011 issued in corresponding Taiwan (R.O.C.) Patent Application No. 98119713 and translation of Search Report (5 pages).

Non-Final Office Action issued Feb. 16, 2012 in related U.S. Appl. No. 12/952,952 (20 pages).

PCT Notification of Transmittal of the International Search Report and the Written Opinion of the International Searching Authority issued May 14, 2012 in corresponding International Application No. PCT/US2011/057278 (10 pages).

Examiner's Report issued Apr. 10, 2012 in related Canadian application No. 2,724,146 (3 pages).

Examiner's Report (and summary thereof) issued in corresponding Chilean application No. 1405-2009 (9 pages).

* cited by examiner

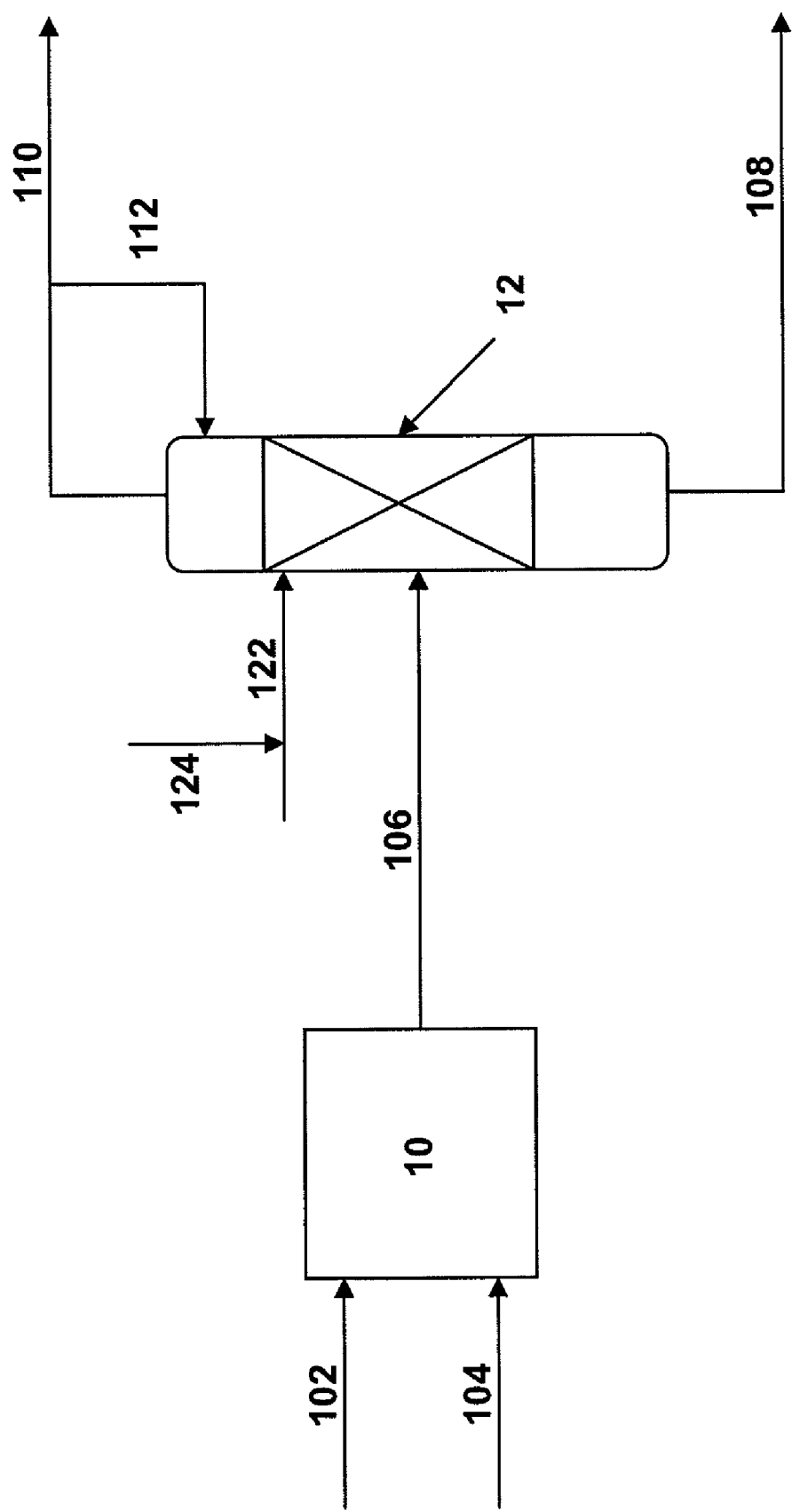

ABSORBER DEMETHANIZER FOR METHANOL TO OLEFINS PROCESS

BACKGROUND OF DISCLOSURE

1. Field of the Disclosure

Embodiments disclosed herein relate generally to a process for converting oxygenates to olefins. In one aspect, embodiments disclosed herein relate to a process for converting methanol to olefins (MTO). In another aspect, embodiments disclosed herein relate to an MTO process including separating and recovering ethylene from an MTO reactor effluent. In yet another aspect, embodiments disclosed herein relate to an MTO process including using a hydrocarbon absorbent to separate and recover ethylene from an MTO reactor effluent. In still another aspect, embodiments disclosed herein relate to the separation and recovery of ethylene from an MTO reactor effluent at conditions to avoid substantial formation of $N_2O_3$.

2. Background

Limited availability and high cost of petroleum sources has led to the increased cost of producing basic commodity chemicals and their derivatives from such petroleum sources. As a result, various alternative competing technologies have been developed and commercially implemented in order to produce these chemicals from non-petroleum sources at a competitive cost.

One such technology involves catalytically converting methanol to olefins (MTO). Methanol is a readily available feedstock, which can be manufactured both from petroleum as well as non-petroleum sources, for example, by fermentation of biomass or from synthesis gas.

A typical MTO process, as disclosed in U.S. Pat. No. 4,499,327, which is hereby incorporated in its entirety, involves contacting methanol with a zeolite catalyst, such as an aluminosilicate, under conditions of temperature and pressure in order to produce light olefins, such as ethylene. Ethylene is an extremely valuable commodity chemical for producing various derivatives, such polyethylene, used in many commercial as well as consumer products and applications.

Before ethylene produced by an MTO process can be sold and used, it is necessary to employ a process which recovers the ethylene component in a desirable, ethylene rich stream by separating it from other components and impurities. For example, depending on the feedstock composition, the reaction conditions, and the extent of side reactions, an MTO effluent can contain other light olefins and diolefins, and light paraffins such as methane. In addition, one particular side reaction that can occur during the MTO process is formation of nitrogen oxides, NO and $NO_2$, commonly referred to as NOx, from nitrogen and oxygen in any entrained air in or nitrogen fed to the MTO reactor system.

One process for the separating and recovering of ethylene from an MTO process effluent involves the use of flash stages and distillation at cryogenic temperatures, as described in U.S. Pat. Nos. 7,166,757 and 4,499,327. As described therein, the current state of the art ethylene recovery and separation processes which dominate the industry involve cryogenic boiling point separation of ethylene and methane at temperatures that may be lower than −90° C. The cryogenic separation can be very expensive due to both the capital cost of the specialized vessel metallurgy and refrigeration equipment, and the operating costs, including compression and cooling for the energy-intensive chill train.

The use of cryogenic temperatures during the processes for treating the MTO process effluent can result in unstable and potentially dangerous operating conditions. For example, the NOx present in the MTO process effluent can react to form $N_2O_3$. Further, it has been found that the $N_2O_3$ formation rate significantly increases with decreasing temperature, thus making a cryogenic process especially susceptible. $N_2O_3$ is a highly oxidative compound, which can form highly unstable and highly reactive gums upon contact with poly-unsaturated compounds, such as butadiene. Even at cryogenic temperatures and at concentrations in the ppb levels, such unstable gums can accumulate and cause dangerous runaway reactions and even explosions.

Accordingly, there exists a need for an improved method of treating an MTO process effluent to separate and recover ethylene and other valuable products that reduces the capital and operating costs and improves the operation safety and stability.

SUMMARY OF THE DISCLOSURE

In one aspect, embodiments disclosed herein relate to a process for the conversion of methanol to olefins, the process including: contacting methanol and at least one of air and nitrogen in a methanol-to-olefins reactor system; recovering an effluent from the methanol-to-olefins reactor system including methanol, dimethyl ether, methane, ethylene, and nitrogen oxides including NO and $NO_2$; and separating the effluent via one or more extractive distillation and/or distillation stages to recover a first fraction including ethylene and a second fraction including methane; wherein the separating comprises operating the one or more extractive distillation and/or distillation stages at temperatures and pressures sufficient to prevent any substantial conversion of nitrogen oxides to $N_2O_3$.

In another aspect, embodiments disclosed herein relate to a process a process for the conversion of methanol to olefins, the process including: feeding at least a portion of a methanol-to-olefins reactor effluent including methane and ethylene to an extractive distillation column; and countercurrently contacting the reactor effluent with at least one $C_2$-$C_4$ hydrocarbon in the extractive distillation column to produce an overheads fraction containing methane and a bottoms fraction containing the at least one $C_2$-$C_4$ hydrocarbon and ethylene.

In another aspect, embodiments disclosed herein relate to a process for the conversion of methanol to olefins, the process including: contacting methanol and at least one of air and nitrogen in a methanol-to-olefins reactor system; recovering an effluent from the methanol-to-olefins reactor system containing methane, ethylene, and nitrogen oxides including NO and $NO_2$; feeding at least a portion of the methanol-to-olefins reactor system effluent to an extractive distillation column; countercurrently contacting the methanol-to-olefins reactor system effluent with at least one $C_2$-$C_4$ hydrocarbon in the extractive distillation column to produce an overhead fraction containing methane and a bottoms fraction containing the at least one $C_2$-$C_4$ hydrocarbon and ethylene; operating the extractive distillation column at conditions sufficient to: (i) absorb ethylene in the at least one $C_2$-$C_4$ hydrocarbon; and (ii) prevent any substantial conversion of the nitrogen oxides to $N_2O_3$.

Other aspects and advantages will be apparent from the following description and the appended claims.

BRIEF DESCRIPTION OF DRAWINGS

FIG. 1 is a simplified flow diagram for an MTO process according to embodiments disclosed herein.

DETAILED DESCRIPTION

In one aspect, embodiments disclosed herein relate to a process for converting an oxygenate to an olefin. In another aspect, embodiments disclosed herein relate to a process for converting methanol to olefins (MTO). In yet another aspect, embodiments disclosed herein relate to an MTO process including separating and recovering ethylene from an MTO reactor effluent. In yet another aspect, embodiments disclosed herein relate an MTO process including using a hydrocarbon absorbent to separate and recover ethylene from an MTO effluent. In still another aspect, embodiments disclosed herein relate to an MTO process including use of a $C_2$-$C_4$ hydrocarbon absorbent to separate and recover ethylene from an MTO effluent in one or more extractive distillation and/or distillation stages at temperatures and pressures sufficient to prevent substantial conversion of nitrogen oxides into $N_2O_3$.

Olefin-containing streams produced, for example, via MTO processes may inevitably contain trace amounts of nitrogen oxides, including NO and $NO_2$. Typically, nitrogen oxides are inert; however, under appropriate conditions, these compounds may further react to form $N_2O_3$, which is highly reactive. For example, even trace amounts, $N_2O_3$ may combine and react with poly-unsaturated olefins, such as butadiene present in an olefin-containing stream, to form highly unstable gum compounds. Such compounds are a major safety and operability concern, as they may cause runaway reactions and even explosions.

As used in embodiments disclosed herein, the term "substantial conversion" in reference to nitrogen oxides refers to the formation and/or accumulation of $N_2O_3$ at levels greater than 10 ppb in some embodiments, greater than 5 ppb in other embodiments, and greater than 1 ppb in yet other embodiments. Conversely, "prevention of any substantial conversion" or like terminology refers to the prevention of the formation and/or accumulation of $N_2O_3$ at levels greater than 10 ppb in some embodiments, greater than 5 ppb in other embodiments, and greater than 1 ppb in yet other embodiments.

At normal temperatures, the rate of $N_2O_3$ formation may be negligible. However, it has been found by the present inventors that the conversion of nitrogen oxides, including NO and $NO_2$, to $N_2O_3$ increases with a decrease in temperature, and may become substantial at cryogenic temperatures, for example, at temperatures of less than $-90°$ C. Therefore, the traditional method for separating ethylene from an olefin-containing stream using cryogenic flash stages and distillation may pose safety and operability concerns.

Using a $C_2$-$C_4$ hydrocarbon absorbent to separate ethylene and higher carbon number products from methane and lights in olefin-containing streams at temperatures sufficient to prevent or reduce levels of $N_2O_3$ formation according to embodiments disclosed herein provides a viable alternative to the traditional cryogenic separation process. In particular, the $C_2$-$C_4$ hydrocarbon absorbent may be used to separate an olefin-containing stream produced, for example, via a methanol-to-olefins process, an ethanol-to-olefins process, or other processes that may produce an effluent containing NOx, methane and other light gases, and having a low hydrogen content.

Processes disclosed herein may be used to convert oxygenates to olefins. In particular, processes disclosed herein may be used to convert methanol to olefins, and to separate and recover ethylene from a methanol-to-olefins reaction effluent. For example, a feedstock containing one or more oxygenated compounds may be converted to one or more olefins. Non-limiting examples of suitable oxygenate compounds include alcohols, including straight and branched chain aliphatic alcohols and their unsaturated counterparts, such as methanol, ethanol, n-propanol and isopropanol; alkyl ethers such as dimethyl ether, diethyl ether, methylethyl ether and di-isopropyl ether; alkyl ketones such as dimethylketone; aldehydes such as formaldehides, dimethylcarbonate and various acids such as acetic acid. In some embodiments, the oxygenate feedstock may include methanol as the main oxygenate compound. In other embodiments, the oxygenated feedstock may consist essentially of methanol.

In addition to oxygenated compounds, such as methanol, the feedstock may contain one or more diluent(s), which are generally non-reactive to the feedstock or the catalyst and are typically used to reduce the concentration of the feedstock. Non-limiting examples of diluents include helium, argon, nitrogen, carbon monoxide, carbon dioxide, water, essentially non-reactive paraffins, such as methane, ethane, and propane, essentially non-reactive aromatic compounds, and mixtures thereof. In some embodiments, a diluent may include at least one of nitrogen and water. In other embodiments, a diluent may consist essentially of nitrogen. Additionally, air may be entrained into the methanol-to-olefins reaction system, for example, due to operation under partial vacuum conditions or as an impurity in one of the feedstock components.

A variety of embodiments for the methanol-to-olefins reaction system may be used. In some embodiments, the methanol-to-olefins reactor system may include a single reaction zone. In other embodiments, the methanol-to-olefins reactor system may comprise multiple reaction zones arranged in series. In some embodiments, the methanol may travel upflow through the one or more reaction zones. In other embodiments, the methanol may travel downflow through the one or more reaction zones.

One or a combination of a variety of reactor types can be used in the methanol-to-olefins reactor system, including, but not limited to: fixed bed reactors; dense, bubbling, riser-type, or slurry-type fluidized bed reactors; boiling point reactors; and catalytic distillation reactors, for example, as described in U.S. Pat. Nos. 4,076,796 and 6,287,522. One of ordinary skill in the art would recognize that other types of reactors can also be used.

The catalyst used in the methanol-to-olefins reactor system may be one of a homogeneous catalyst or a heterogeneous catalyst. In some embodiments, the catalyst may be a zeolite or mole sieve catalyst. In one specific embodiment, the catalyst may be a crystalline aluminosilicate zeolite catalyst, such as those disclosed in U.S. Pat. Nos. 4,062,905, 4,079,095, 3,911,041, and 4,049,573. One of ordinary skill in the art would recognize that other types of catalysts can also be used.

The methanol-to-olefins reaction process can be conducted over a wide range of temperatures, such as in the range from approximately 200° C. to approximately 1000° C. In some embodiments, the temperature of the methanol-to-olefins reaction system may be between approximately 200° C. and approximately 700° C. In other embodiments, the temperature of the methanol-to-olefins reaction system may be between approximately 300° C. and approximately 600° C. In yet other embodiments, the temperature of the methanol-to-olefins reaction system may be between approximately 350° C. and approximately 550° C.

Similarly, the process can be conducted over a wide range of pressures including autogenous pressure. Typical partial pressures of the feedstock, exclusive of any diluent therein employed in the process, is in the range from approximately 0.1 kPaa to approximately 5 MPaa. In some embodiments, the pressure of the methanol-to-olefins reaction system may be between approximately 5 kPaa and approximately 1 MPaa. In other embodiments, the pressure of the methanol-to-olefins reaction system may be between approximately 20 kPaa and approximately 500 kPaa.

The olefins produced by a process for producing olefins from oxygenates, for example a methanol-to-olefins process, according to embodiments disclosed herein may include one or more of $C_2$ to $C_{30}$ olefins and/or diolefins. In some embodiments, the olefins produced may include one or more of $C_2$ to $C_8$ olefins. In other embodiments, the olefins produced may include one or more of $C_2$ to $C_6$ olefins. In yet other embodiments, the olefins produced may include one or more of $C_2$ to $C_4$ olefins, for example, ethylene and propylene. In still other embodiments, the olefins produced may consist essentially of ethylene.

In some embodiments, the concentration of ethylene in the methanol-to-ethylene reactor effluent may be at least approximately 5 mole percent. In other embodiments, the concentration of ethylene in the methanol-to-ethylene reactor effluent may be at least approximately 10 mole percent. In yet other embodiments, the concentration of ethylene in the methanol-to-ethylene reactor effluent may be at least approximately 20 mole percent. In still other embodiments, the concentration of ethylene in the methanol-to-ethylene reactor effluent may be at least approximately 30 mole percent.

A methanol-to-olefins reaction may also produce non-olefin products, including but not limited to, paraffins, acetylenes, ethers, and esters. For example, a methanol-to-olefins reaction effluent may include methane, ethane, propane, n-butane, isobutane, n-butene, isobutene, butadiene, dimethyl ether and water. The presence and concentrations of these by-products may vary depending, for example, on the feedstock quality, the type and size of reactor, the reaction conditions, and the type and condition of the catalyst used.

In some embodiments, the concentration of methane in the methanol-to-ethylene reactor effluent may be less than approximately 30 mole percent. In other embodiments, the concentration of methane in the methanol-to-ethylene reactor effluent may be less than approximately 20 mole percent. In yet other embodiments, the concentration of methane in the methanol-to-ethylene reactor effluent may be less than approximately 10 mole percent. In still other embodiments, the concentration of methane in the methanol-to-ethylene reactor effluent may be less than approximately 5 mole percent. In other embodiments, the concentration of methane in the methanol-to-ethylene reactor effluent may be less than approximately 2 mole percent.

Other side reactions may also occur in the methanol-to-olefins reaction system. For example, the diluent nitrogen and/or nitrogen present in the entrained air can react with the oxygen present in entrained air or the oxygenates inside the methanol-to-olefins reaction system to form nitrogen oxides, including NO and $NO_2$. As discussed above, if exposed to cryogenic conditions, these oxides may further react to form $N_2O_3$, a highly undesirable compound from both a safety and an operability standpoint. One of ordinary skill in the art would recognize that nitrogen oxides can also form in other processes for producing olefins from other oxygenates, such as ethers and other alcohols.

In order to recover ethylene of sufficient purity, the methanol-to-olefins reactor effluent may undergo one or more separation stages. For example, it may be desired or necessary to separate ethylene from various reactants and products, including but not limited to, ethers and alcohols, carbon dioxide, water, methane, and other reactants, reaction products, and diluents.

In some embodiment, at least a portion of the methanol-to-olefins reactor effluent may be fed to an extraction system for removing any methanol and/or ethers contained therein using an aqueous solvent, such as water or glycol. An aqueous fraction having an increased concentration of methanol and ethers may be recovered from the extraction system. A hydrocarbon phase comprising methane and ethylene, and lean in methanol and ethers, may be recovered from the reactor effluent in the extraction system. The hydrocarbon phase may then be sent for further component separation(s). In some embodiments, the methanol-to-olefins reactor effluent may be compressed prior to any further separation(s).

Carbon dioxide that may be present in the methanol-to-olefins reactor effluent may also require removal. For example, an olefin product specification may require removal of carbon dioxide from the methanol-to-olefins reactor effluent. Further, exposure of the carbon dioxide containing stream to below-sublimation temperatures may result in equipment damage and frozen piping. Methods commonly known and used in the industry, such as caustic solution treatment or amine absorption, may be used to remove $CO_2$ from the methanol-to-olefins reactor effluent. In some embodiments, the reactor effluent may be contacted with a caustic solution to separate at least a portion of the carbon dioxide present in the reactor effluent. If necessary, the reactor effluent may be compressed prior to the carbon dioxide removal stage.

The presence of water in methanol-to-olefins reaction effluent can lead to a number of problems. For example, cooling and/or compressing the reaction effluent may result in formation of water condensate that can damage equipment and freeze pipes. Therefore, dehydration of the reactor effluent to remove water using one of a number of techniques commonly used in the industry may be required or may be optionally performed based on process schemes and temperatures employed. In some embodiments, a molecular sieve dryer may be used for separating at least a portion of the water, drying the reactor effluent. In other embodiments, a chemical desiccant such as glycol may be used for drying the reactor effluent. In yet other embodiments, a portion of the water in the reactor effluent may be condensed and the remaining effluent may be dried. Other dehydration techniques commonly known and used in the industry may also be used. If necessary, the reactor effluent may be compressed prior to the water removal stage.

A particularly challenging separation is that of ethylene from methane and lights, including nitrogen oxides, within the methanol-to-olefins reactor effluent due to low component boiling points. As discussed above, currently available separation methods, such as cryogenic flash stages and distillation, may lead to formation of undesirable $N_2O_3$ and may require a high degree of dehydration and $CO_2$ removal in order to meet olefin product specification and/or to avoid pipe freeze and equipment damage.

It has been found that a hydrocarbon absorbent, such as a $C_2$-$C_4$ hydrocarbon absorbent, can be effectively used as an absorbent to separate and recover ethylene and higher olefinic hydrocarbons from an MTO reaction effluent at non-cryogenic temperatures. For example, an MTO reaction effluent including ethylene and methane can be contacted with a hydrocarbon absorbent in an extraction distillation system, whereby at least a portion of the ethylene is absorbed by the hydrocarbon absorbent.

In some embodiments, the hydrocarbon absorbent may be a $C_2$ to $C_4$ hydrocarbon, for example, including at least one of ethane, propane, propylene, n-butane, isobutane, n-butene, and isobutene. In other embodiments, the hydrocarbon absorbent may consist essentially of propane.

In some embodiments, the extraction distillation system may include one or more extractive distillation and/or distillation stages. For example, the methanol-to-olefins reactor effluent may be contacted with the hydrocarbon absorbent in one or more extractive distillation and/or distillation stages arranged in series within a single column or in a series of multiple columns.

The one or more extractive distillation and/or distillation stages may comprise trays and/or packing for providing a sufficient surface for the contacting. In some embodiments, the methanol-to-olefins reactor effluent and hydrocarbon absorbent may be contacted counter-currently in the extraction distillation system. In other embodiments, the methanol-to-olefins reactor effluent and hydrocarbon absorbent may be contacted co-currently in the extraction distillation system.

In some embodiments, the extraction distillation system may be operated at an overheads temperature of approximately −90° C. or greater. In other embodiments, the extraction distillation system may be operated at an overheads temperature of approximately −50° C. or greater. In yet other embodiments, the extraction distillation system may be operated at an overheads temperature of approximately −40° C. or greater. In yet other embodiments, the extraction distillation system may be operated at an overheads temperature of approximately −20° C. or greater. In still other embodiments, the extraction distillation system may be operated at an overheads temperature of approximately −10° C. or greater. In other embodiments, the extraction distillation system may be operated at an overheads temperature of approximately 0° C. or greater.

In general, the overheads pressure inside the extraction distillation system may be maintained at a level required for the distillation and as required for absorption of ethylene into the hydrocarbon absorbent. In some embodiments, the overheads pressure inside the extraction distillation system may be in the range from approximately 0.01 MPag to 10 MPag. In other embodiments, the overheads pressure inside the extraction distillation system may be in the range from approximately 0.1 MPag to 4 MPag. In yet other embodiments, the overheads pressure inside the extraction distillation system may be in the range from approximately 0.5 MPag to 3 MPag. In still other embodiments, the overheads pressure inside the extraction distillation system may be in the range from approximately 0.5 MPag to 1 MPag.

In some embodiments, at least approximately 70 percent of ethylene molecules may be absorbed and recovered from the extraction distillation system as a bottoms fraction along with the hydrocarbon absorbent. In other embodiments, at least approximately 80 percent of ethylene molecules may be absorbed and recovered from the extraction distillation system as a bottoms fraction along with the hydrocarbon absorbent. In yet other embodiments, at least approximately 90 percent of ethylene molecules may be absorbed and recovered from the extraction distillation system as a bottoms fraction along with the hydrocarbon absorbent. In still other embodiments, at least approximately 95 percent of ethylene molecules may be absorbed and recovered from the extraction distillation system as a bottoms fraction along with the hydrocarbon absorbent. In other embodiments, at least approximately 99 percent of ethylene molecules may be absorbed and recovered from the extraction distillation system as a bottoms fraction along with the hydrocarbon absorbent.

The bottoms fraction may be further separated to recover ethylene. In some embodiments, the bottoms fraction may be separated to form an ethylene fraction and a hydrocarbon fraction including at least one of $C_2$-$C_4$ hydrocarbon heavier than ethylene. In other embodiments, the bottoms fraction may be separated to form light hydrocarbon fraction containing ethylene and ethane, and a hydrocarbon fraction containing at least one $C_3$-$C_4$ hydrocarbon.

In some embodiments, the concentration of the carried over hydrocarbon absorbent recovered in the overheads fraction along with methane from the extraction distillation system is less than approximately 30 mole percent. In other embodiments, the concentration of the carried over hydrocarbon absorbent recovered in the overheads fraction along with methane from the extraction distillation system is less than approximately 15 mole percent. In yet other embodiments, the concentration of the carried over hydrocarbon absorbent recovered in the overheads fraction along with methane from the extraction distillation system is less than approximately 10 mole percent. In still other embodiments, the concentration of the carried over hydrocarbon absorbent recovered in the overheads fraction along with methane from the extraction distillation system is less than approximately 5 mole percent.

Embodiments disclosed herein maintain pressure and temperature inside the extraction distillation system sufficient to prevent any significant formation of $N_2O_3$ from nitrogen oxides, including NO and $NO_2$, present in the methanol-to-olefins reactor effluent. As discussed above, it has been found that the rate of $N_2O_3$ formation becomes significant at temperatures below approximately −90° C. Thus, by avoiding cryogenic process temperatures of approximately −90° C. and below, for example, by using a hydrocarbon absorption process according to embodiments disclosed herein, the formation of $N_2O_3$ may be prevented or significantly reduced.

Referring now to FIG. 1, a process for converting methanol to olefins according to embodiments disclosed herein is illustrated. For simplicity purposes, auxiliary equipment has been omitted from the FIGURE. One of ordinary skill in the art would recognize that other equipment and devices, including but not limited to, pumps, compressors, heat exchangers, drums, vessels, reactors, flow lines, valves, and control loops, can also be used. For example, other features not illustrated in FIG. 1, including but not limited to, external heat exchange loops on the extractive distillation column and other features that may be used and could appear in a Process & Instrumentation Diagram (P&ID) for embodiments disclosed herein, are presumed.

Methanol may be supplied to a methanol-to-olefins reactor system 10 via flow line 102. Air and/or nitrogen may be entrained with the methanol feed or added through vacuum leaks, thus supplying nitrogen to the process. Nitrogen may also be used as a diluents and may be supplied to the methanol-to-olefins reactor system 10 via flow line 104. Methanol 102 may be contacted with a catalyst at conditions of temperature and pressure inside the methanol-to-olefins reactor system 10 to produce ethylene. A methanol-to-olefins reactor effluent may be recovered from the methanol-to-olefins reactor system 10 via flow line 106. As discussed above, depending on the specific process requirements, the methanol-to-olefins reactor effluent 106 may undergo various separations to remove one or more of ethers and alcohols, carbon dioxide, and water from the reactor effluent 106 (optional separation processes not shown in FIG. 1). Those of ordinary skill in the art will appreciate that nitrogen or air may be introduced to the reaction system via one or more of vacuum leaks, feed impurities, and diluent feeds, by way of example, but other techniques may be used as well.

The methanol-to-olefins reactor effluent in flow line 106 may then be contacted with a hydrocarbon absorbent fed via flow line 122 in the extraction distillation system 12. In some embodiments, recycle hydrocarbon absorbent make-up may be added via flow line 124. As the hydrocarbon absorbent traverses the column, ethylene is absorbed by the hydrocarbon absorbent. The hydrocarbon absorbent and the absorbed ethylene may be recovered from the extraction distillation system 12 as a bottoms fraction via flow line 108. The methane may be recovered from the extraction distillation system 12 as an overheads fraction via flow line 110.

In some embodiments, at least a portion of the overheads fraction 110 may be returned to the extraction distillation system 12 as reflux via flow line 112. In other embodiments, a reflux ratio of the reflux 112 to the overheads fraction 110 may be used to control the composition of the overheads fraction 110.

The bottoms fraction 108 may be further treated (not shown in FIG. 1) to form and separate an ethylene fraction containing ethylene and a hydrocarbon fraction containing the hydrocarbon absorbent. At least a portion of the hydrocarbon fraction may be recycled to the extraction distillation system 12 as a hydrocarbon absorbent make-up 124.

In some embodiments where the hydrocarbon absorbent is propane and the overheads fraction 108 from the extraction distillation system 12 comprises propane, at least a portion of the overheads fraction 108 may be used as fuel. For example, both the methane and the propane in the overheads fraction 108 may be sent to a fuel header. In other embodiments, at least a portion of the propane in the overheads fraction 108 may be compressed and recovered.

Advantages of processes according to embodiments disclosed herein may include improved operational safety and stability due to minimization of $N_2O_3$ formation from nitrogen oxides. As discussed above, trace amounts of nitrogen oxides, including NO and $NO_2$, present in the MTO reaction effluent can react to form $N_2O_3$, a highly oxidative compound which can in turn react with heavy unsaturated compounds, such as butadiene, present in the MTO reaction effluent to form unstable and highly reactive gums. Such gums, even at cryogenic temperatures and at ppb concentrations, can accumulate and cause dangerous runaway reactions and even explosions. As the rate of $N_2O_3$ formation drastically increases with decreasing temperature, and thus the cryogenic processes at temperatures lower than approximately −90° C. currently used for separation and recovery of ethylene from the MTO reaction effluent are a major safety concern. In contrast, Applicants have found that using hydrocarbon absorption to separate and recover ethylene from an MTO reaction effluent at temperatures of −90° C. or higher is sufficient to prevent formation of $N_2O_3$.

Another advantage of processes according to embodiments disclosed herein may include reduced capital equipment cost. For example, the traditional cryogenic process, commonly referred to as the "chill train," requires specialized metallurgies and complicated refrigeration systems, including vessels, compressors, heat exchangers, circulation piping, and refrigerant costs. In contrast, as the present process is not conducted at cryogenic temperatures, less expensive metallurgy can be used and a number of equipment items associated with the chill train may be eliminated.

Processes according to embodiments disclosed herein may also advantageously reduce operating costs. For example, the energy costs of the refrigeration compression associated with the traditional cryogenic separation system may be considerably higher than those associated with a non-cryogenic extractive distillation process.

Still another possible advantage of recovering ethylene and/or heavier olefins from an MTO effluent according to embodiments disclosed herein may be that any portion of the $C_2$-$C_4$ hydrocarbon absorbent, such as propane, entrained with the methane distillate, does not require additional compression and recovery, and instead may be sent directly to the process plant fuel header or otherwise may be used as a fuel.

For example, in other ethylene production processes, such as in catalytic cracking, the value of any residual $C_2$-$C_4$ hydrocarbons may be too high to be sent to fuel; requiring additional compression and recovery facilities to recover the valued products. In contrast, the $C_2$-$C_4$ hydrocarbons have no further use in the MTO reaction process, and thus may economically be sent to fuel.

Recovery of ethylene and/or heavier olefins from an MTO effluent according to embodiments may also reduced capital and operating costs due to reduced separation requirements for other non-olefin components present in a methanol-to-olefins reactor effluent. For example, limiting the process design to operating temperatures of −90° C. and higher, and in some embodiments to temperatures of −40° C. and higher, may eliminate the need for expensive ethylene and/or methane refrigeration loops commonly used in ethylene plant cryogenic separation schemes. In contrast, using propane and/or propylene refrigeration to provide chilling for a methane-to-olefins process according to embodiments disclosed herein may substantially reduce capital investment costs and improve reliability.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for the conversion of methanol to olefins, the process comprising:
   feeding at least a portion of a methanol-to-olefins reactor effluent comprising methane and ethylene to an extractive distillation column;
   countercurrently contacting the reactor effluent with a hydrocarbon solvent consisting essentially of propane in the extractive distillation column to produce an overheads fraction comprising methane and a bottoms fraction comprising the hydrocarbon solvent and ethylene.

2. The process of claim 1, further comprising operating the extractive distillation column at an overheads temperature of −90° C. or greater.

3. The process of claim 1, further comprising operating the extractive distillation column at an overheads temperature of −40° C. or greater.

4. The process of claim 1, further comprising operating the extractive distillation column at an overheads pressure in the range from about 1 to about 4 MPag.

5. The process of claim 1, further comprising separating the bottoms fraction to form an ethylene fraction and a hydrocarbon fraction consisting essentially of propane.

6. The process of claim 5, further comprising recycling at least a portion of the hydrocarbon fraction to the extractive distillation column.

7. The process of claim 1, further comprising separating the bottoms fraction to form a light hydrocarbon fraction comprising ethylene and ethane, and a hydrocarbon fraction consisting essentially of propane.

8. The process of claim 1, further comprising
   contacting the reactor effluent with an aqueous solvent comprising at least one of water and glycol to remove any methanol or ethers contained therein to form an aqueous fraction having an increased concentration of methanol and ethers and a hydrocarbon phase comprising methane and ethylene; and
   feeding the hydrocarbon phase to the extractive distillation column as the at least a portion of the reactor effluent.

9. The process of claim 1, further comprising:

at least one of:
    contacting the reactor effluent with a caustic solution to separate at least a portion of carbon dioxide;
    contacting the reactor effluent with a molecular sieve dryer to separate at least a portion of water;
recovering a reactor effluent having a reduced concentration of at least one of carbon dioxide and water; and
feeding the reactor effluent having a reduced concentration of at least one of carbon dioxide and water as the at least a portion of the methanol-to-olefins reactor effluent to the extractive distillation column.

10. The process of claim 1, further comprising:
condensing and recycling at least a portion of the overheads fraction to the extractive distillation column as a reflux.

11. The process of claim 1, wherein the overheads fraction further comprises propane, the process further comprising using at least a portion of the overheads fraction as a fuel.

12. A process for the conversion of methanol to olefins, the process comprising:
    contacting methanol and at least one of air and nitrogen in a methanol-to-olefins reactor system;
    recovering an effluent from the methanol-to-olefins reactor system comprising methane, ethylene, and nitrogen oxides including NO and $NO_2$,
    feeding at least a portion of the methanol-to-olefins reactor system effluent to an extractive distillation column;
    countercurrently contacting the methanol-to-olefins reactor system effluent with a hydrocarbon solvent consisting essentially of propane in the extractive distillation column to produce an overhead fraction comprising methane and a bottoms fraction comprising propane and ethylene;
    operating the extractive distillation column at conditions sufficient to
        i. absorb ethylene in the hydrocarbon solvent; and
        ii. prevent any substantial conversion of the nitrogen oxides to $N_2O_3$.

13. The process of claim 12, further comprising operating the extractive distillation column at an overheads temperature of −90° C. or greater.

14. The process of claim 12, further comprising operating the extractive distillation column at an overheads temperature of −40° C. or greater.

15. The process of claim 12, further comprising operating the extractive distillation column at an overheads pressure in the range from about 1 to about 4 MPag.

16. The process of claim 12, further comprising fractionating the bottoms fraction to form an ethylene fraction and a hydrocarbon fraction consisting essentially of propane.

17. The process of claim 16, further comprising recycling at least a portion of the hydrocarbon fraction to the extractive distillation column.

18. The process of claim 12, further comprising separating the bottoms fraction to form a light hydrocarbon fraction comprising ethylene and ethane, and a hydrocarbon fraction consisting essentially of propane.

19. The process of claim 12, further comprising
    contacting the methanol-to-olefins reactor system effluent with an aqueous solvent comprising at least one of water and glycol to remove any methanol or ethers contained therein to form an aqueous fraction having an increased concentration of methanol and ethers and a hydrocarbon phase comprising methane and ethylene; and
    feeding the hydrocarbon phase to the extractive distillation column as the at least a portion of the methanol-to-olefins reactor system effluent.

20. The process of claim 12, further comprising:
at least one of:
    contacting the reactor effluent with a caustic solution to separate at least a portion of carbon dioxide;
    contacting the reactor effluent with a molecular sieve dryer to separate at least a portion of water;
recovering a reactor effluent having a reduced concentration of at least one of carbon dioxide and water; and
feeding the reactor effluent having a reduced concentration of at least one of carbon dioxide and water as the at least a portion of the methanol-to-olefins reactor effluent to the extractive distillation column.

21. The process of claim 12, further comprising:
condensing and recycling at least a portion of the overheads fraction to the extractive distillation column as a reflux.

22. The process of claim 12, wherein the overheads fraction further comprises propane, the process further comprising using at least a portion of the overheads fraction as a fuel.

23. A process for the conversion of methanol to olefins, the process comprising:
    contacting methanol and at least one of air and nitrogen in a methanol-to-olefins reactor system;
    recovering an effluent from the methanol-to-olefins reactor system comprising methanol, dimethyl ether, methane, ethylene, and nitrogen oxides including NO and $NO_2$,
    separating the effluent via one or more extractive distillation and distillation stages to recover a first fraction comprising ethylene and a second fraction comprising methane, wherein the extractive distillation is performed with a solvent consisting essentially of propane; and
    wherein the separating comprises operating the one or more extractive distillation and/or distillation stages at temperatures and pressures sufficient to prevent any substantial conversion of nitrogen oxides to $N_2O_3$.

* * * * *